(12) United States Patent
Sekiguchi

(10) Patent No.: US 6,550,916 B1
(45) Date of Patent: Apr. 22, 2003

(54) OPHTHALMOLOGICAL APPARATUS

(75) Inventor: Kyoji Sekiguchi, Utsunomiya (JP)

(73) Assignee: Canon Kabushiki Kaisha, Tokyo (JP)

( * ) Notice: Subject to any disclaimer, the term of this patent is extended or adjusted under 35 U.S.C. 154(b) by 186 days.

(21) Appl. No.: 09/599,951

(22) Filed: Jun. 23, 2000

(30) Foreign Application Priority Data

Jul. 8, 1999 (JP) .......................................... 11-194900

(51) Int. Cl.[7] ................................................. A61B 3/10
(52) U.S. Cl. ...................................................... 351/221
(58) Field of Search ................................. 351/205, 206, 351/221, 243, 246; 382/117

(56) References Cited

U.S. PATENT DOCUMENTS

| 4,572,627 A | 2/1986 | Madate et al. ............... 351/206 |
| 4,660,946 A | 4/1987 | Nakamura et al. ........... 351/212 |
| 4,666,269 A | 5/1987 | Nakamura et al. ........... 351/212 |
| 4,690,525 A | 9/1987 | Kobayashi et al. .......... 351/206 |
| 4,697,895 A | 10/1987 | Sekiguchi et al. ........... 351/243 |
| 4,710,003 A | 12/1987 | Masuda et al. ............... 351/212 |
| 4,762,410 A | 8/1988 | Sekiguchi et al. ........... 351/206 |
| 4,878,750 A | 11/1989 | Sekiguchi et al. ........... 351/212 |
| 5,530,493 A | * 6/1996 | Suzuki ........................ 351/206 |
| 5,589,899 A | 12/1996 | Maeda ......................... 351/245 |
| 5,751,396 A | 5/1998 | Masuda et al. ............... 351/212 |

\* cited by examiner

Primary Examiner—George Manuel
(74) Attorney, Agent, or Firm—Fitzpatrick, Cella, Harper & Scinto

(57) ABSTRACT

An ophthalmological apparatus includes an illuminator for illuminating an eye to be examined; an image pickup device for obtaining the image of the illuminated examined eye; a signal converter for converting a signal from the image pickup device into digital data; and a controller for controlling a system, which controller limits a predetermined operation of other than the image pickup device and the signal converter while the signal converter is performing a conversion operation. The ophthalmological apparatus can take a high-quality photographic image by preventing the occurrence of noise or by reducing noise.

67 Claims, 4 Drawing Sheets

OPHTHALMOLOGICAL APPARATUS

BACKGROUND OF THE INVENTION

1. Field of the Invention

The present invention relates to an ophthalmological apparatus, such as a digital fundus camera, for taking photographic images of an eye to be examined in ophthalmological clinics, etc.

2. Description of the Related Art

FIG. 4 is a block diagram of the construction of a typical digital fundus camera. Inside a fundus camera 1, an objective lens 2 and a perforated mirror 3 are disposed along the optical path in front of an eye E to be examined, an observation photographing optical system 4 is disposed in the direction of transmittance through the perforated mirror 3, and an illumination optical system 5 is disposed in the direction of the incidence of the perforated mirror 3. These optical systems each include an illumination light source, and a power supply 11 is provided therefor. In the rear of the observation photographing optical system 4, an image pickup device 6, composed of two-dimensional image pickup elements, is mounted. The image pickup device 6 is connected to a video amplifier 7, a converter 8, and an image storage device 9 in that order. A controller 10 controls the entire system.

With such a construction, a light beam from a halogen lamp light source of the fundus illumination optical system 5 is projected from below the perforated mirror 3. Then, the light beam is reflected to the left in a portion peripheral to the perforated mirror 3, passes through the objective lens 2, and irradiates the fundus Er of the eye E to be examined. The light beam reflected from the fundus Er passes through the objective lens 2. and passes, to the right, through the opening in the center of the perforated mirror 3. Focusing adjustment is performed thereon in the observation photographing optical system 4, and the light beam is formed into an image in the imaging plane of the image pickup device 6. The image pickup device 6 outputs an analog video signal, and amplification, clamping, and band limitation are performed on the analog video signal in the video amplifier 7. In the converter 8, the analog video signal is converted into digital image data, and this image data is stored in the image storage device 9. The power supply 11 is a power supply for the illumination light source.

A photographer performs alignment between the eye E to be examined and the optical system, and presses a photographing switch. Thereupon, a strobe light source for taking pictures, disposed in the fundus illumination optical system 5, emits light as a result of a predetermined timing between the image pickup device 6 and a video cycle being taken. Then, the power supply 11 starts charging immediately after the strobe light emission. The light beam from the strobe light source illuminates the fundus Er of the eye E to be examined in a manner similar to the above-mentioned observation light, and the light reflected from the fundus Er is captured by the image pickup device 6 in a similar manner. This is stored as a fundus image signal and is output as an image signal at the next video cycle. This video signal is converted into digital data by the converter 8, such as an A/D converter, is stored in the image storage device 9, and is displayed or stored.

However, during the period in which the image picked up by the image pickup device 6 is output, that is, during the period in which the converter 8 performs the conversion operation, there is a possibility that high-frequency noise occurring due to the operation in the image storage device 9, the power supply 11, etc., enters the signal system and the ground line of the converter 8, exerting an adverse influence on digital conversion. In particular, during control for controlling large amounts of power, much noise occurs. In the converter 8, since a video signal is digitally converted at 8 to 10 bits, if the analog signal is assumed to be at 1 V at the peak-point voltage, a very small voltage of 0.97 to 3.9 mV per bit must be handled. At this time, since the accuracy is ½ bits, it is necessary to reduce noise to less than half of this voltage. In particular, in the photographing of the fundus, since the original S/N ratio of the image is not good, the problem of noise cannot be ignored. In the fundus image which is greatly affected by noise, noise may become an obstacle to accurately performing examination of very small blood vessels and the optic nerve.

SUMMARY OF THE INVENTION

An object of the present invention is to provide an ophthalmological apparatus which solves the above-described problems and which is capable of taking high-quality pictures by preventing the occurrence of noise or by reducing noise.

According to one aspect, the present invention that achieves at least one of these objectives relates to an ophthalmological apparatus comprising an illuminator configured and positioned to project light toward an eye to be examined, thereby illuminating the eye to be examined. The apparatus also comprises an image pickup device configured and positioned to receive light from the illuminated, examined eye, to form an image of the illuminated, examined eye, and to generate a signal representing the image. The apparatus further comprises a signal converter, connected to the image pickup device to receive the signal generated by the image pickup device. The signal converter is configured to convert the received signal to digital data by a conversion operation. The apparatus also includes at least one additional element, and a controller, connected to the illuminator, the image pickup device, the signal converter, and the at least one additional element. The controller receives signals from image pickup device, the signal converter, and the at least one additional element. The controller transmits control signals to the illuminator, the image pickup device, the signal converter, and the one additional element, respectively controlling the illuminator, the image pickup device, the signal converter, and the at least one additional element. The controller also generates a limit signal to limit a predetermined operation of at least one of the illuminator and the at least one additional element while the signal converter is performing a conversion operation.

According to another aspect, the present invention that achieves at least one of these objectives relates to an ophthalmological apparatus comprising illuminating means for illuminating an eye to be examined, imaging means for forming an image of the illuminated eye and for generating a signal representing the image, converting means for converting the signal to digital data by a conversion operation, at least one additional means for performing an additional function, and control means for controlling the illuminating means, the imaging means, the converting means, and the at least one additional means and for limiting a predetermined operation of at least one of the illuminating means and the at least one additional means while the signal converting means is performing the conversion operation.

According to still another aspect, the present invention that achieves at least one of these objectives relates to a method of examining the eye comprising the steps of illuminating an eye to be examined, forming an image of the illuminated eye and for generating a signal representing the image, converting the signal to digital data by a conversion operation, the digital data containing information to enable an examiner to examine the eye, performing an additional operation in examining the eye, and limiting a predetermined operation of at least one of the illuminating step and the performing step while the signal converting step is performing the conversion operation to reduce noise generated during the at least one of the illuminating step and the performing step.

According to still another aspect, the present invention that achieves at least one of these objectives relates to a noise reducing device for an ophthalmological apparatus comprising an illuminator configured and positioned to project light toward an eye to be examined, thereby illuminating the eye to be examined, an image pickup device configured and positioned to receive light from the illuminated, examined eye, to form an image of the illuminated, examined eye, and to generate a signal representing the image, a signal converter, connected to the image pickup device to receive the signal generated by the image pickup device, the signal converter being configured to convert the received signal to digital data by a conversion operation, and at least one additional element. The noise reducing device comprises a controller, connected to the illuminator, the image pickup device, the signal converter, and the at least one additional element. The controller receives signals from the image pickup device, the signal converter, and the at least one additional element. The controller also transmits control signals to the illuminator, the image pickup device, the signal converter, and the one additional element, respectively controlling the illuminator, the image pickup device, the signal converter, and the at least one additional element. In addition, the controller generates a limit signal to limit a predetermined operation of at least one of the illuminator and the one additional element while the signal converter is performing a conversion operation.

According to still another aspect, the present invention that achieves at least one of these objectives relates to a method of reducing noise produced during an eye examination with an ophthalmological apparatus that illuminates the eye to be examined, forms an image of the illuminated, examined eye, and generates a signal representing the image, converts the signal to digital data by a conversion operation, and performs at least one additional process with at least one additional element. The noise reducing method comprises the steps of limiting a predetermined operation of at least one of the illuminating operation and the performing of at least one additional process by the ophthalmological apparatus step while the ophthalmological apparatus converts the signal to digital data, thereby reducing noise generated during at least one of the illuminating operation and the performing of at least one additional process.

The above and further objects, aspects and novel features of the invention will become more apparent from the following detailed description when read in conjunction with the accompanying drawings.

DETAILED DESCRIPTION OF THE PREFERRED EMBODIMENT

Figure 1:
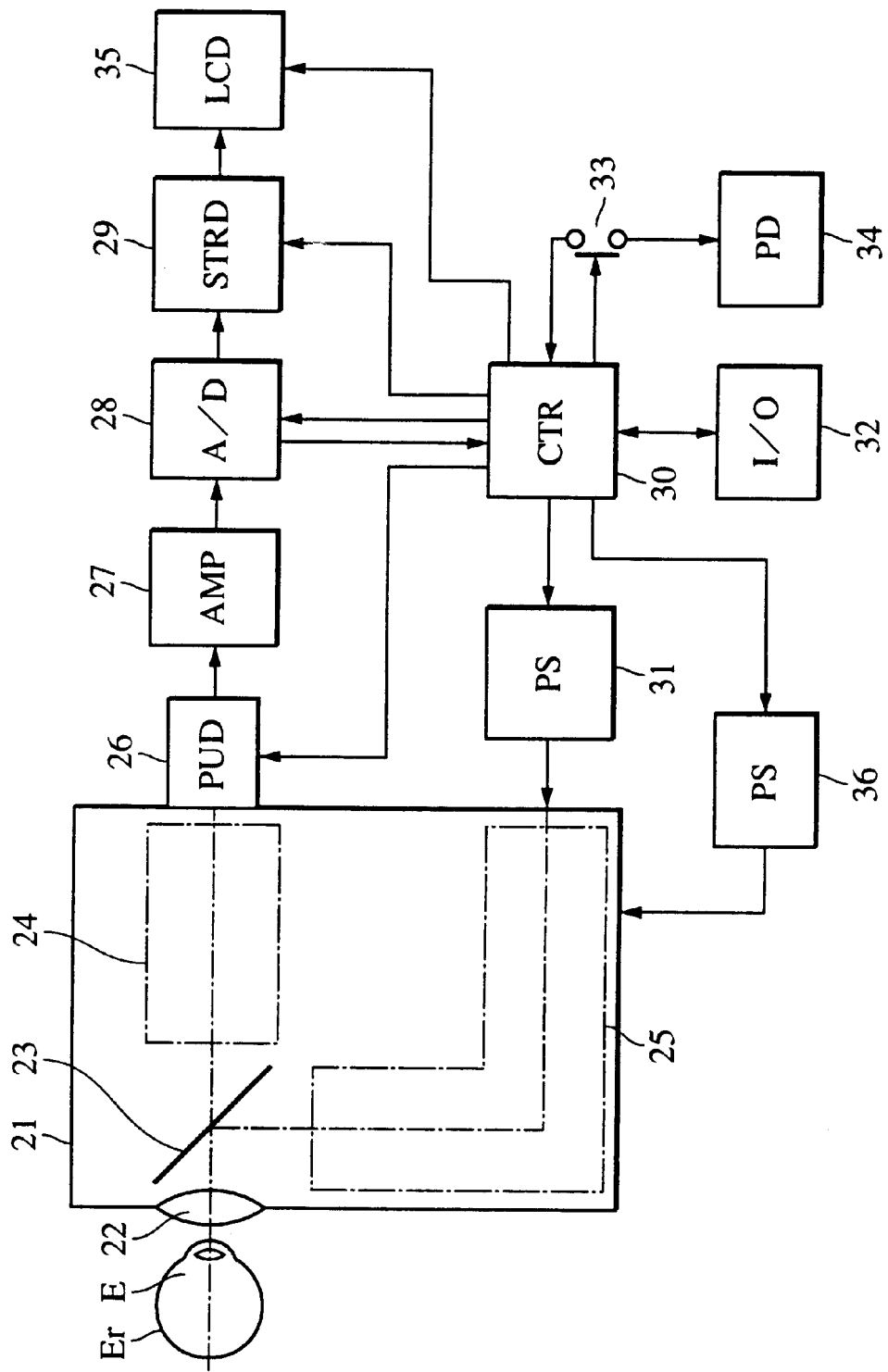
FIG. 1 is a block diagram of an ophthalmological photographing apparatus according to an embodiment of the present invention.

A preferred embodiment of the present invention is described below with reference to FIGS. 1 to 3. FIG. 1 Is a block diagram of an ophthalmological photographing apparatus according to an embodiment of the present invention. Inside a fundus camera 21, an objective lens 22 and a perforated mirror 23 are disposed along the optical path in front of an eye E to be examined, an observation photographing optical system 24 is disposed in the direction of the transmittance through the perforated mirror 23, and an illumination optical system 25 is disposed in the direction of the incidence of the perforated mirror 23. In the rear of the observation photographing optical system 24, an image pickup device 26, composed of two-dimensional image pickup elements, is mounted.

Figure 4:
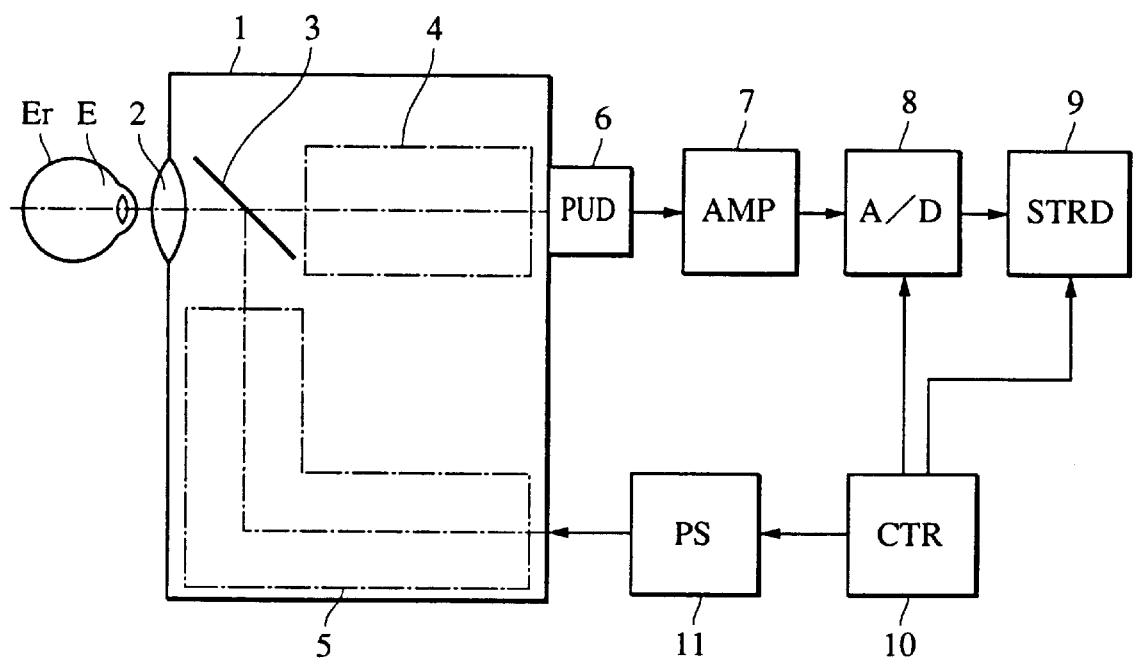
FIG. 4 is a block diagram of a conventional ophthalmological photographing apparatus.

The output side of the image pickup device 26 is connected to a video amplifier 27 for amplifying a video signal, a converter (A/D converter) 28 for converting the amplified analog video signal to digital image signal data, and an image storage device 29 in that order. The image storage device 29 includes a memory for storing digitally converted image data, a fixed hard disk for the purpose of storage, or a removable disk which can be carried. Also, a liquid-crystal display (LCD) 35 for reproducing and displaying the stored image data is connected to the image storage device 29. A controller 30 controls the overall operations of the image pickup device 26, the converter 28, the image storage device 29, the LCD 35, a power supply 31 for supplying power for a light source (not shown) of the illumination optical system 25 for the purpose of illumination, an I/O (input/output) device 32, a switch 33, a system power supply 36, etc. Since the photographing procedure has been described in the example of FIG. 4, and since the photographing procedure is the same here, a description thereof is omitted here to avoid duplicated description.

While the converter 28 is operating, from the converter 28, a limit signal, for limiting predetermined functions and operations that can become a noise source inside the apparatus, is generated. The controller 30 recognizes the limit signal from the converter 28, and limits the operation of each section in order to reduce noise while the converter 28 is operating. Specifically, the controller 30 controls the supply of inverter power for driving a backlight inside the LCD 35 by, for example, stopping the supply of inverter power and by, for example, controlling the turning on and off (or controlling the turning on and off of the power supply of the image-storage-device hard disk itself) of the motor for the hard disk incorporated in the image storage device 29. Furthermore, the controller 30 controls the power supply 31 and individually comprises a control circuit of an illumination light source (not shown) of the illumination optical system 25, a charging circuit of a strobe light source for taking pictures (not shown), and a light amount control circuit (not shown) of a halogen lamp (not shown) of the observation photographing optical system 24 for observation so that these light sources are controlled individually. That is, while the converter 28 is operating, the operation of the power supply 31 is limited as required, so that, for example, the illumination light source is switched off, the charging control of the strobe is stopped, or the halogen lamp is switched off. Also, the controller 30 controls the I/O devices 32, such as operation switches including a fundus photographing switch, and input/output switches of various types of indicator lamps, and also controls an external apparatus 34, such as a memory device, a computer, and a network apparatus, which are connected externally via the switch 33. That is, while the converter 28 is operating, the switch 33 is opened in accordance with a limit signal, so that the electrical connection with the external apparatus 34 is disconnected. Also, the controller 30 performs control such that the system power supply 36 for the entire apparatus, different from the power supply 31, is switched to either one of a switching power supply (alternating current from an electrical outlet or other source) and a battery power supply. Also, the controller 30 has a function for decreasing the driving clock frequency of a microcomputer, incorporated within itself, which is not active or a function for switching the microcomputer to a sleep state, in accordance with a limit signal from the converter 28.

Figure 2:
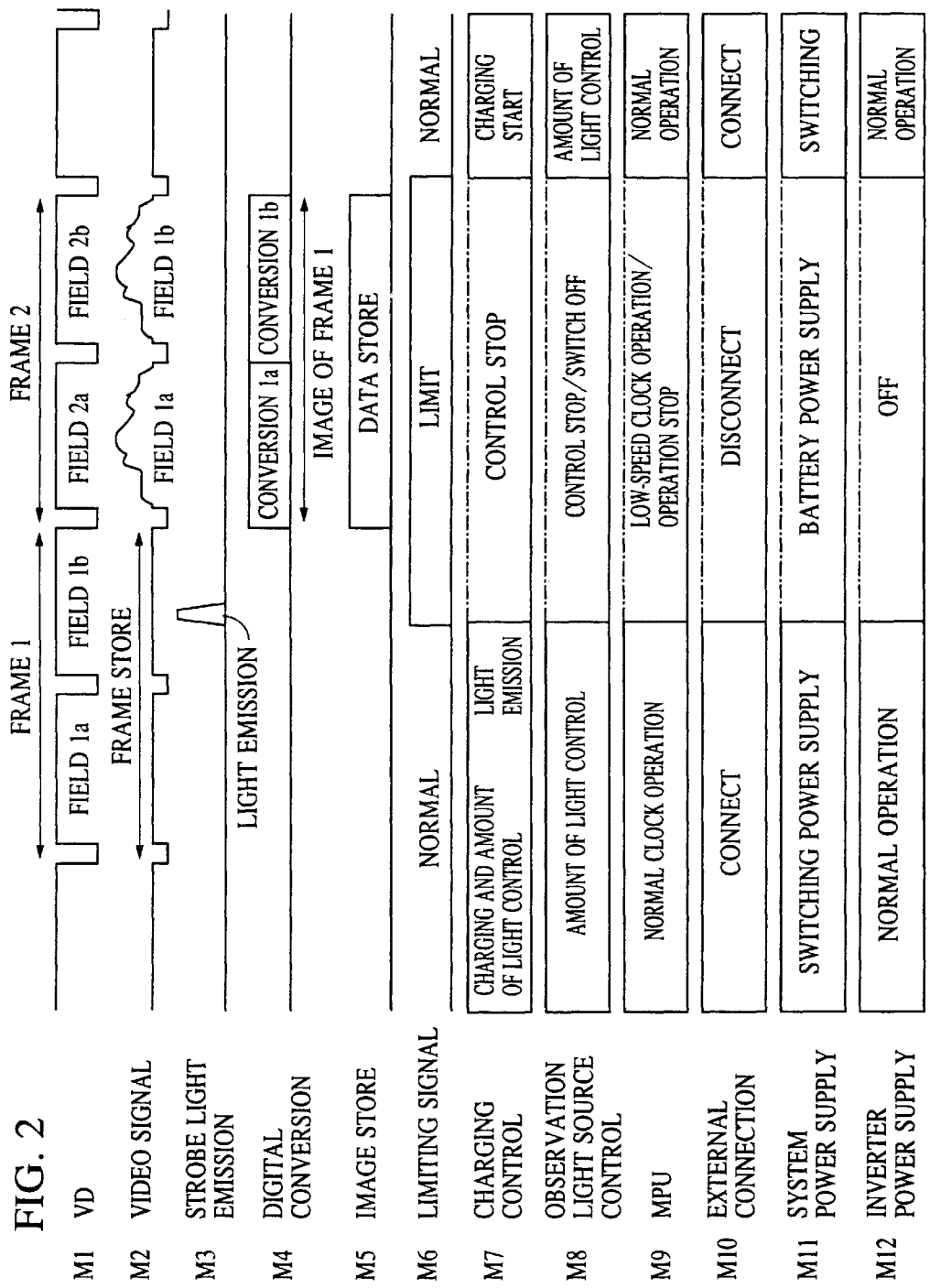
FIG. 2 is a timing chart of a frame store mode.

FIG. 2 is a timing chart for when the apparatus operates in a frame store mode, in which the horizontal axis is a time axis. A vertical synchronization signal M1 is also contained in the video signal output from the image pickup device 26 and can also be extracted directly from the image pickup device 26. A video signal M2 is a signal output from the image pickup device 26. When pictures are not being taken, an observation image is output, and this image is displayed on the LCD 35. Strobe light emission for the purpose of taking pictures is performed in response to the strobe light receiving a light-emission trigger signal of signal M7 in accordance with a timing signal M3 generated by controller 30. Since the image pickup device 26 is operating in the frame store mode, the light-emission trigger signal is generated at a timing at which two fields 1a and 1b of the vertical synchronization signal M1 are in a stored state. That is, in FIG. 2, strobe light emission is performed in the period of the second field 1b of frame 1 of the signal M1. The photographed image of the examined eye E, obtained by this light emission, is output as a video signal in the next frame 2. The signal of the field 1a is output initially, and then the signal of the field 1b is output. These signals are converted into digital signals in sequence, and this converted data is stored in the image storage device 29.

A comparison between a timing signal M4, generated by controller 30, at which conversion is performed by the converter 28 (during conversion 1a conversion of the data in field 1a is performed and during conversion 1b conversion of data in field 1b is performed) and a timing signal M5, generated by controller 30, at which the image storage device 29 stores data shows that the timing signal M5 is delayed slightly by an amount of the time required for storage. However, this delay is only several milliseconds to several tens of milliseconds so that it can be ignored (and is not shown in FIG. 2). A limit signal M6 is output from converter 28 at a timing synchronized with the operation of the converter 28. That is, while the converter 28 is performing a conversion operation, the limit signal M6 becomes a limit signal (1), otherwise it is a normal signal (0). A signal M7 is an operation signal of a charging control circuit of the strobe. The signal M7 is a charging-and-amount-of light-control signal instructing the charging of the strobe until a short time before conversion by converter 28. Shortly before conversion occurs, signal M7 becomes a light-emission trigger signal triggering light emission of the strobe when the strobe-light emission signal M3 peaks. Once light emission of the strobe occurs and before conversion by converter 28 begins, signal M7 becomes a control-stop signal stopping emission and charging of the strobe until after the digital conversion and storage instructed by signals M4 and M5, at which point signal M7 again becomes a charging signal instructing charging of the strobe. A signal M8 is an operation signal of a control circuit for the observation light source. Signal M8 is an amount-of-light control signal controlling the amount of light emitted by and instructing light emission by the observation light source up to the time that light emission from the strobe occurs and before conversion by converter 28 begins. When light emission of the strobe occurs and conversion by converter 28 begins, M8 becomes a control-stop/switch-off signal instructing turned off of the observation light source until signal M7 again instructs charging of the strobe and converter 8 ends conversion, at which point M8 again becomes an amount-of-light control signal causing light emission by the observation light source. A signal M9 is an operation signal of a microcomputer, incorporated in the controller 30. Signal M9 is a normal-clock-operation signal instructing the microcomputer in controller 30 to operate according to a normal clock operation at a normal clock speed before conversion by converter 28 and the light emission from the strobe. Signal M9 becomes a low-speed-clock-operation/operation-stop signal instructing the microcomputer to operate at a low clock speed or to stop operating entirely once light is emitted from the strobe and before converting by converter 28 occurs. Signal M9 remains a low-speed-clock-operation/ operation-stop signal until the strobe begins charging again and converter 28 stops conversion. Signal M9 again becomes a normal-clock operation signal again instructing the microcomputer to perform according to a normal clock operation when the strobe begins charging again and converter 28 stops conversion. A signal M10 is a timing signal for connection with the external apparatus 34. Signal M10 is a connect signal, instructing connection with an external apparatus 34 during charging of the strobe before the strobe emits light and before conversion by converter 28, becomes a disconnect signal instructing disconnection from external device 34 once the strobe emits light and converter 28 begins conversion and until the strobe begins charging again and the converter stops conversion, and becomes a connect signal again once the strobe begins charging again the converter stops conversion. A signal M11 is an operation signal for the system power supply. Signal M11 is a switching-power-supply signal during charging of the strobe before the strobe emits light and before the converter 28 begins conversion, instructing the apparatus to connect to a switching power supply, such as an AC outlet. Signal M11 becomes a battery-power-supply signal instructing the apparatus to connect to a battery power supply once the strobe emits light and before converter 28 begins conversion and remains a battery-power-supply signal until the strobe starts charging again and converter 28 stops conversion, and again becomes a switching-power supply signal during charging of the strobe and after converter 28 stops conversion. A signal M12 is an operation signal for the inverter power supply (not shown) for the backlight of the LCD 35. Signal M12 is a normal-operation signal during charging of the strobe before the strobe emits light and before conversion by converter 28, instructing the supply of power to the backlight of the LCD 35, becomes an off signal once the strobe emits light and before the converter begins conversion, instructing the turning-off of the power supply to the backlight of LCD 35, and remains an off signal until the strobe starts charging again and converter 28 stops conversion, and becomes a normal-operation signal once the strobe starts charging again and converter 28 stops conversion.

Figure 3:
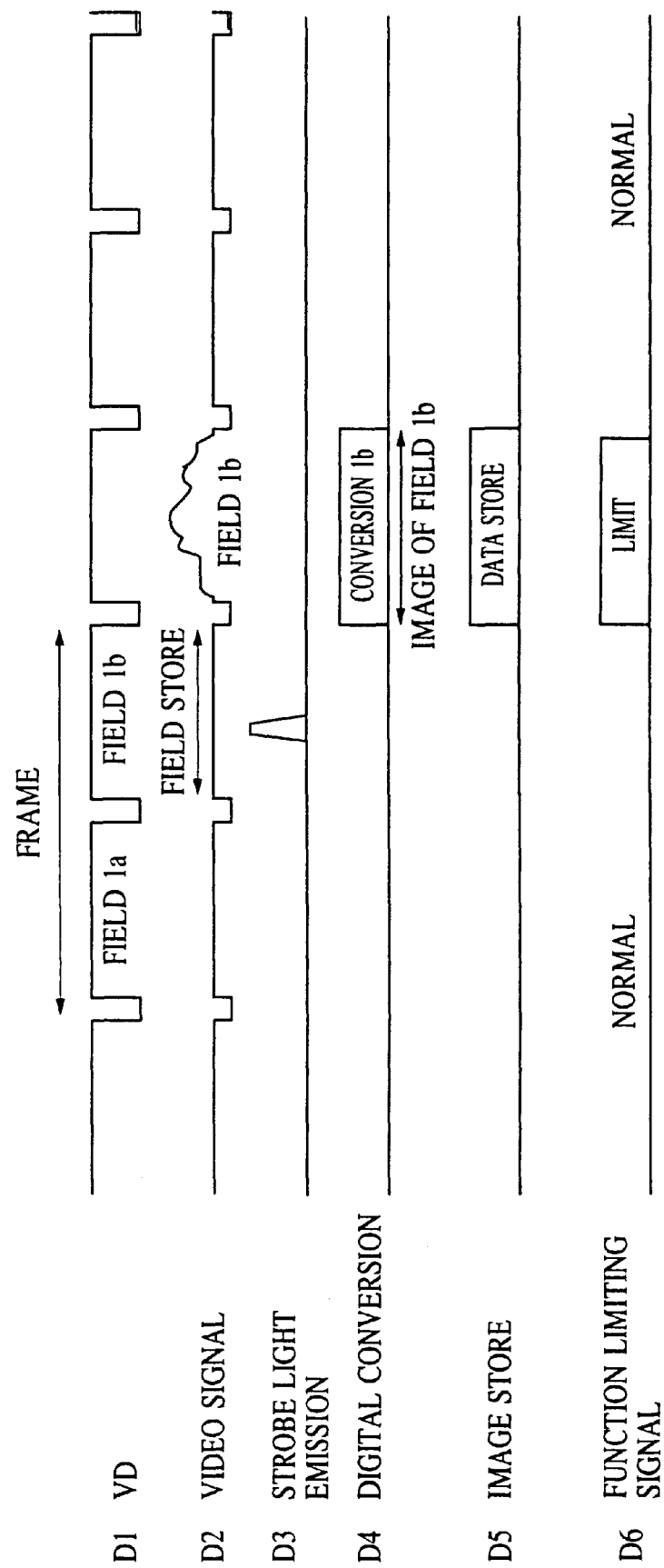
FIG. 3 is a timing chart of a field store mode.

FIG. 3 is a timing chart when the apparatus operates in a field-store mode, in which the horizontal axis is a time axis.

Timings are each shown at which a vertical synchronization D1 from the image pickup device 6, a video signal D2, a strobe light emission signal D3 for the strobe light source, a timing digital-conversion signal D4 for digital conversion, a timing image-store signal D5 at which digitally converted data is stored, and a function-limiting signal D6 are output. In the field store mode, since a signal is output in a field next to the stored field, the time required for digital conversion is shorter than that in FIG. 2.

Thus, the digital-conversion signal D4 converts only the field 1b of the analog video signal M2 to a digital signal. During this conversion, signal D5 becomes a data-store signal to store the converted video signal and signal D6 becomes a function-limiting signal.

In FIG. 2, when the strobe light source is made to emit light in accordance with the light-emission trigger signal of the timing signal M3, the converter 28 operates, causing the limit signal M6 to be converted from "normal (0)" to "limit (1)". In order that noise from each section of the apparatus is minimized while the converter 28 is operating, the controller 30 generates signals M7–M12, as shown in FIG. 2, in order to limit the operation of each section of the apparatus. The controller 30 need not limit all these operations, and may limit only some of these operations.

The signal M7, before the photographing operation, causes a switching circuit (not shown) of a high voltage to operate so as to charge a capacitor (not shown) with a necessary high-voltage charge, which capacitor causes the strobe light source to emit light. After the light emission, the signal M7 becomes a control-stop signal instructing that the charging operation be immediately stopped to prevent an occurrence of noise up to the time the photographed image is changed into a digital form by converter 28. Then, after the digitization, charging for the next photographing operation is started in response to signal M7 becoming a charging-start signal. The halogen lamp light source for observation also controls the power passing therethrough by switching and controlling the voltage applied to the halogen lamp to adjust the amount of emitted light, and since noise during switching affects digital conversion, the powering of the halogen lamp is stopped during digital conversion in response to signal M8 becoming a control-stop/switch-off signal. The controller 30 operates in synchronization with a clock signal from a clock oscillator (not shown). Since the controller 30 generally operates in accordance with a high-frequency signal of 8 to 20 MHz, when access to a ROM, a RAM, and an interface is made, a high-speed pulse is output in a data bus (not shown), an address bus (not shown), and a control signal line (not shown), causing much noise to occur. Since these noises are reduced if the clock frequency is reduced, the frequency of an inactive microcomputer inside the controller 30 is decreased to a lower-limit-operation frequency of the controller 30 in a period in which the limit signal M6 is output in response to the signal M9 becoming a low-speed-clock-operation/operation-stop signal, or the operation in that period is stopped in the period in which the limit signal M6 is output in response to signal M9 becoming a low-speed-clock-operation/operation-stop signal.

In a case in which the apparatus is connected to the external apparatus 34 and is used, since noise from the external apparatus 34 enters from a signal line and a ground line, the connection with the external apparatus 34 is disconnected by the switch 33 as required in a period in which the limit signal M6 is output in response to signal M10 becoming a disconnect signal. Also, the apparatus is ordinarily driven by the switching power supply of system power supply 36, and switching to the battery power supply of system power supply 36 is performed while the limit signal M6 is being output in response to signal M11 becoming a battery-power-supply signal so that occurrence of noise is minimized. Also, while limit signal M6 is being output, the inverter power supply for the backlight of the LCD 35 is turned off in accordance with the signal M12 becoming an off signal.

In FIG. 2, the limit signal M6 is output from the time when the strobe emits light. Alternatively, the limit signal M6 may be output from the time of the start of frame 2 or may be output earlier if the image of frame 2 is output earlier. In a case in which it takes time from when the limit signal M6 is received by controller 30 until the operation mode of controller 30 is switched so that controller 30 generates one or more of signals M7–M12, and this M7–M12-signal generation state becomes a stable state, the signal M6 may be output slightly earlier than noted above to make allowance for these delays. In a case in which the limit signal M6 is turned off (i.e., it becomes a "normal (0)" signal), if the digitization of the image signal has been terminated, the limit signal M6 may be turned off at any time. The above operation similarly applies to FIG. 3.

Even when the image pickup device 26 operates in a progressive scan mode, basically, the limit signal M6 is output while the image is output and is digitized, so that a function limitation is applied to a block of the device in which substantial noise occurs. In a case in which the image pickup device 26 changes its analog output signal directly into digital form, if a signal indicating the timing at which digitization is performed is output from the image pickup device 26, this signal may be used in a similar manner as the limit signal M6.

The digital fundus camera which has thus been described limits the operation of noise generation sources other than the converter and the image pickup device when an analog signal from the image pickup device is converted into a digital signal by the converter. This makes it possible to reduce noise when a photographic signal is digitally recorded and makes it possible to obtain a high-quality digital image.

Many different embodiments of the present invention may be constructed without departing from the spirit and scope of the present invention. It should be understood that the present invention is not limited to the specific embodiment described in this specification. To the contrary, the present invention is intended to cover various modifications and equivalent arrangements included within the spirit and scope of the invention as hereafter claimed. The scope of the following claims is to be accorded the broadest interpretation so as to encompass all such modifications, equivalent structures and functions.

What is claimed is:

1. An ophthalmological apparatus comprising:
   an illuminator configured and positioned to project light toward an eye to be examined, thereby illuminating the eye to be examined;
   an image pickup device configured and positioned to receive light from the illuminated, examined eye, to form an image of the illuminated, examined eye, and to generate a signal representing the image;
   a signal converter, connected to said image pickup device to receive the signal generated by said image pickup device, said signal converter being configured to convert the received signal to digital data by a conversion operation;

at least one additional element; and a controller, connected to said illuminator, said image pickup device, said signal converter, and said at least one additional element, said controller receiving signals from said image pickup device, said signal converter, and said at least one additional element, said controller transmitting control signals to said illuminator, said image pickup device, said signal converter, and said one additional element, respectively controlling said illuminator, said image pickup device, said signal converter, and said at least one additional element, and said controller generating a limit signal to limit a predetermined operation of said at least one additional element while said signal converter is performing the conversion operation and to prevent illumination of the illuminator while said signal converter performs the conversion operation.

2. An ophthalmological apparatus according to claim 1, wherein said illuminator comprises a light source and a light-source power supply connected to said light source, wherein said controller is connected to said light-source power supply, wherein said controller transmits said limit signal to said light-source power supply instructing said light-source power supply to turn off the light source while said signal converter is performing a conversion operation.

3. An ophthalmological apparatus according to claim 2, wherein said illuminator comprises at least one of a light source configured and positioned to generate light to illuminate the eye to be examined, a strobe light source configured and positioned to generate strobe light appropriate for taking of a picture of the eye, and an observation light source configured and positioned to generate light to illuminate the eye with light appropriate for observing the eye.

4. An ophthalmological apparatus according to claim 1, further comprising a storage device, connected to said signal converter and to said controller, said storage device storing the digital data produced by said signal converter, wherein said controller controls the operation of the storage device while said signal converter is performing a conversion operation.

5. An ophthalmological apparatus according to claim 1, further comprising a display device, connected to said controller, wherein said display device displays images picked up by said image pickup device, wherein said limit signal generated by said controller is a signal instructing the display device to limit its operation while said signal converter is performing a conversion operation.

6. An ophthalmological apparatus according to claim 5, further comprising a power supply connected to said display device and supplying power to said display device, the limit signal generated by said controller instructing said power supply to stop the supply of power to said display device while said signal converter is performing a conversion operation.

7. An ophthalmological apparatus according to claim 1, further comprising a switch, and an external apparatus connected to said controller via said switch, wherein said limit signal generated by said controller is a signal instructing the opening of said switch to electrically disconnect said external apparatus from said ophthalmological apparatus while said signal converter is performing a conversion operation.

8. An ophthalmological apparatus according to claim 1, further comprising a system power supply, connected to said controller, including a switching power supply and a battery power supply, wherein said switching power supply supplies power to said ophthalmological apparatus when said signal converter is not performing a conversion operation, and said limit signal instructs said battery power supply to supply power to said ophthalmological apparatus while said signal converter is performing a conversion operation.

9. An ophthalmological apparatus according to claim 1, wherein said controller comprises a microcomputer, wherein the limit signal generated by said controller instructs the limiting of the operation of said microcomputer while said signal converter is performing a conversion operation.

10. An ophthalmological apparatus according to claim 9, wherein said limit signal generated by said controller instructs the lowering of the clock speed of said microcomputer.

11. An ophthalmological apparatus according to claim 9, wherein said limit signal generated by said controller instructs the stopping of the operation of said microcomputer.

12. An ophthalmological apparatus according to claim 1, wherein said image pickup device obtains a fundus image of the examined eye.

13. An ophthalmological apparatus according to claim 1, wherein said signal converter generates a signal-converter limit signal when said converter performs a conversion operation, instructing said controller to generate said limit signal.

14. An ophthalmological apparatus according to claim 13, wherein said illuminator comprises an observation light source, wherein said apparatus further comprises:

a strobe light source, connected to said controller;

a strobe-light-source charging circuit, connected to said strobe light source and said controller, configured to charge said strobe light source;

an observation-light-source charging circuit, connected to said observation light source and said controller, configured to power said observation light source;

a microcomputer, being part of said controller;

a switch;

an external device, connected via said switch to said controller;

a system power supply, connected to said controller, including a switching power supply and a battery power supply;

a display device, connected to said controller, configured to display images picked up by said image pickup device; and an inverter power supply, connected to said display device and to said controller, configured to supply power to said display device;

wherein said controller generates a plurality of limit signals in response to receiving said converter-signal limit signal from said signal converter, wherein one of said controller limit signals instructs said strobe-light-source charging circuit to stop charging said strobe light source while said converting means is performing said conversion operation, wherein another one of said controller limit signals instructs said observation-light-source charging circuit to stop powering said observation light source while said signal converting means is performing said conversion operation, wherein another one of said controller limit signals instructs said microcomputer to either operate at a reduced clock frequency, lower than that used when said signal converter is not performing a conversion operation, or stop its operation while said signal converting means is performing said conversion operation, wherein another one of said controller limit signals instructs said switch to electrically disconnect said external device from said controller while said converting means is performing said conversion operation, wherein another one of said controller limit signals instructs said system power supply to switch to the use of said battery power supply to supply power to said ophthalmological apparatus while said signal converting means is performing said conversion operation, and wherein another one of said controller limit signals instructs said inverter power to stop supplying power to said display device while said signal converting means is performing said conversion operation.

15. An ophthalmological apparatus comprising:

illuminating means for illuminating an eye to be examined;

imaging means for forming an image of the illuminated eye and for generating a signal representing the image;

converting means for converting the signal to digital data by a conversion operation;

at least one additional means for performing an additional function; and control means for controlling said illuminating means, said imaging means, said converting means, and said at least one additional means and for limiting a predetermined operation of said at least one additional means while said signal converting means is performing said conversion operation and for preventing illumination of said illuminating means while said converting means performs said conversion operation.

16. An ophthalmological apparatus according to claim 15, wherein said illuminating means comprises means for generating light and means for powering said light generating means, wherein said control means turns off said powering means while said converting means is performing a conversion operation.

17. An ophthalmological apparatus according to claim 16, wherein said illuminating means comprises means for generating a strobe light for use in photographing the eye.

18. An ophthalmological apparatus according to claim 15, further comprising storing means for storing the digital data produced by said converting means, wherein said control means controls the operation of said storing means while said signal converting means is performing a conversion operation.

19. An ophthalmological apparatus according to claim 15, further comprising display means for displaying images picked up by said imaging means, wherein said control means limits the operation of said display means while said converting means is performing a conversion operation.

20. An ophthalmological apparatus according to claim 19, further comprising power supplying means for supplying power to said display means, wherein said control means stops the supply of power from said power supplying means to said display means while said signal converting means is performing a conversion operation.

21. An ophthalmological apparatus according to claim 15, further comprising:

external means, external to said apparatus, for performing at least one function relating to said ophthalmological apparatus; and means for connecting and disconnecting said external means to said ophthalmological apparatus, wherein said control means controls said connecting and disconnecting means to electrically disconnect said external means from said ophthalmological apparatus while said signal converting means is performing a conversion operation.

22. An ophthalmological apparatus according to claim 15, further comprising system power supply means for supplying power to said apparatus, wherein said system power supply means comprises switching power supply means for supplying power to said apparatus from a switching power supply and battery power supply means for supplying battery power to said apparatus, wherein said switching power supply means supplies power to said ophthalmological apparatus when said converting means is not performing a conversion operation, and said battery power supply means supplies battery power to said ophthalmological apparatus while said signal converting means is performing a conversion operation.

23. An ophthalmological apparatus according to claim 15, wherein said control means comprises microcomputer means for performing computer operations, wherein said control means limits the operation of said microcomputer means while said converting means is performing a conversion operation.

24. An ophthalmological apparatus according to claim 23, wherein said control means comprises means for limiting the operation of said microcomputer means by lowering of the clock speed of said microcomputer means.

25. An ophthalmological apparatus according to claim 23, wherein said control means comprises means for limiting the operation of said microcomputer means by stopping of the operation of said microcomputer means.

26. An ophthalmological apparatus according to claim 15, wherein said imaging means comprises means for obtaining a fundus image of the examined eye.

27. An ophthalmological apparatus according to claim 15 wherein said illuminating means comprises means for generating observation light, wherein said apparatus further comprises:

strobe light source means for emitting strobe light;

strobe-light-source charging means for charging said strobe light source means;

observation-light-source charging means for supplying power to said observation light generating means;

microcomputer means for performing computer operations, being part of said control means;

external means, external to said apparatus, for performing an operation related to said apparatus;

connecting and disconnecting means for connecting and disconnecting said external means to and from said apparatus;

system power supply means for supplying switching power and battery power to said apparatus;

display means for displaying images formed by said imaging means; and means for supplying power to said display means;

wherein said control means comprises means for controlling said strobe-light-source charging means to stop charging said strobe light source while said converting means is performing said conversion operation, wherein said control means comprises means for controlling said observation-light-source charging means to stop charging said observation light generating means while said converting means is performing said conversion operation, wherein said control means comprises means for controlling said microcomputer means to either operate at a reduced clock frequency, lower than that used when said converting means is not performing a conversion operation, or stop its operation while said converting means is performing said conversion operation, wherein said control means comprises means for controlling said connecting and disconnecting means to electrically disconnect said external device means from said apparatus while said converting means is performing said conversion operation, wherein said control means comprises means for controlling said system power supply means to supply said ophthalmological apparatus with battery power while said converting means is performing said conversion operation, and wherein said control means comprises means for controlling said means for supplying power to said display means to stop supplying power to said display means while said converting means is performing said conversion operation.

28. A method of examining the eye comprising the steps of:

illuminating an eye to be examined;

forming an image of the illuminated eye and for generating a signal representing the image;

converting the signal to digital data by a conversion operation, the digital data containing information to enable an examiner to examine the eye;

performing an additional operation in examining the eye; and limiting a predetermined operation of at least one of said illuminating step and said performing step while said converting step is performing said conversion operation to reduce noise generated during said at least one of said illuminating step and said performing step.

29. A method according to claim 28, wherein said illuminating step comprises the steps of supplying power to a light source and emitting light with the light source, wherein said limiting step limits the power supplied in said power supplying step to the light source while said signal converting step is performing a conversion operation.

30. A method according to claim 29, wherein the light source is a strobe light source, and wherein limiting step comprises the step of limiting the power supplied to said strobe light source.

31. A method according to claim 28, further comprising the step of storing the digital data produced by said converting step.

32. A method according to claim 28, further comprising the step of displaying images formed in said forming step, wherein said limiting step limits the operation of said displaying step while said converting step is performing a conversion operation.

33. A method according to claim 32, wherein said displaying step displays the images with a display device, said method further comprising the step of supplying power to said display device, wherein said limiting step stops the supply of power to said display device while said signal converting step is performing a conversion operation.

34. A method according to claim 28, wherein said illuminating, forming, converting, performing, and limiting steps are performed with an ophthalmological apparatus, said method further comprising the steps of:

performing an operation relating to the examining of the eye with an external device, external to said ophthalmological apparatus; and electrically disconnecting said external device from said ophthalmological apparatus while said signal converting step is performing a conversion operation.

35. A method according to claim 28, further comprising the steps of:

using alternating current electrical power to perform at least one of said illuminating step, said forming step, said converting step, said performing step, and said control step while said signal converting step does not perform a conversion operation; and using battery power to perform said at least one of said illuminating step, said forming step, said converting step, said performing step, and the control step while said signal converting step is performing a conversion operation.

36. A method according to claim 28, wherein at least one of said illuminating step, said forming step, said converting step, said performing step, and said control step are controlled with a microcomputer, and wherein said limiting step limits the operation of the microcomputer means while said signal converting step is performing a conversion operation.

37. A method according to claim 36, wherein said limiting step lowers the clock speed of the microcomputer while said signal converting step is performing a conversion operation.

38. A method according to claim 37, wherein said limiting step stops the operation of the microcomputer while said signal converting step is performing a conversion operation.

39. A method according to claim 28, wherein said forming step forms a fundus image of the examined eye.

40. A method according to claim 28, wherein said converting step is performed with a signal converter, wherein said limiting step is performed with a controller, wherein said method further comprises the step of: instructing the controller with the signal converter to perform said limiting step while said signal converting step is performing said conversion operation.

41. A method according to claim 40, wherein said illuminating, forming, converting, performing, and limiting steps are performed by an ophthalmological apparatus, wherein said illuminating step is performed by an observation light source charged by an observation light source charger and a strobe light source charged by a strobe light source charger, wherein said illuminating, forming, converting, performing, and limiting steps are controlled by a microcomputer, wherein said ophthalmological apparatus also includes a switch connecting and disconnecting an external device thereto, a system power supply supplying switching power and battery power to said apparatus, a display device displaying images formed by said forming step, and a power supply supplying power to the display device, wherein said limiting step comprises the steps of:

stopping the charging of the strobe light source by the strobe light source charger while said signal converting step is performing said conversion operation, stopping the charging of the observation light source by said observation light source charger while said signal converting step is performing said conversion operation, limiting the operation of the microcomputer to either operate at a reduced clock frequency, lower than that used when said converting step is not performing a conversion operation, or stop its operation while said signal converting step is performing said conversion operation, electrically disconnecting the external device from said apparatus while said signal converting step is performing said conversion operation, supplying the ophthalmological apparatus with battery power while said signal converting step is performing said conversion operation, and stopping the supply of power to the display device while said signal converting step is performing said conversion operation.

42. A noise reducing device for an ophthalmological apparatus comprising an illuminator configured and positioned to project light toward an eye to be examined, thereby illuminating the eye to be examined, an image pickup device configured and positioned to receive light from the illuminated, examined eye, to form an image of the illuminated, examined eye, and to generate a signal representing the image, a signal converter, connected to the image pickup device to receive the signal generated by the image pickup device, the signal converter being configured to convert the received signal to digital data by a conversion operation, and at least one additional element, said noise reducing device comprising:

a controller, connected to the illuminator, the image pickup device, the signal converter, and the at least one additional element, said controller receiving signals from the image pickup device, the signal converter, and the at least one additional element, said controller transmitting control signals to the illuminator, the image pickup device, the signal converter, and the one additional element, respectively controlling the illuminator, the image pickup device, the signal converter, and the at least one additional element, and said controller generating a limit signal to limit a predetermined operation of at least one of the illuminator and the one additional element while the signal converter is performing a conversion operation.

43. A device according to claim 42, wherein the illuminator comprises a light source and a light-source power supply connected to the light source, wherein said controller is connected to the light-source power supply, and wherein said controller transmits said limit signal to the light-source power supply instructing the light-source power supply to turn off the light source while the signal converter is performing a conversion operation.

44. A device according to claim 42, wherein the illuminator comprises at least one of a light source configured and positioned to generate light to illuminate the eye to be examined, a strobe light source configured and positioned to generate strobe light appropriate for taking of a picture of the eye, and an observation light source configured and positioned to generate light to illuminate the eye with light appropriate for observing the eye.

45. A device according to claim 42, wherein the ophthalmological apparatus further comprises a storage device, connected to the signal converter and to said controller, the storage device storing the digital data produced by the signal converter, wherein said controller controls the operation of the storage device while the signal converter is performing a conversion operation.

46. A device according to claim 42, wherein the ophthalmological apparatus further comprises a display device, connected to said controller, wherein the display device displays images picked up by the image pickup device, wherein said limit signal generated by said controller is a signal instructing the display device to limit its operation while the signal converter is performing a conversion operation.

47. A device according to claim 46, wherein the ophthalmological apparatus further comprises a power supply connected to the display device and supplying power to the display device, wherein the limit signal generated by said controller instructs the power supply to stop the supply of power to the display device while the signal converter is performing a conversion operation.

48. A device according to claim 42, wherein the ophthalmological apparatus further comprises a switch, and an external apparatus connected to said controller via the switch, wherein said limit signal generated by said controller is a signal instructing the opening of the switch to electrically disconnect the external apparatus from the ophthalmological apparatus while the signal converter is performing a conversion operation.

49. A device according to claim 42, wherein the ophthalmological apparatus further comprises a system power supply, connected to said controller, including a switching power supply and a battery power supply, wherein the switching power supply supplies power to the ophthalmological apparatus when the signal converter is not performing a conversion operation, wherein said controller controls the system power supply so that the battery power supply supplies battery power to the ophthalmological apparatus while the signal converter is performing a conversion operation.

50. A device according to claim 42, wherein said controller comprises a microcomputer, wherein the limit signal generated by said controller instructs the limiting of the operation of the microcomputer while the signal converter is performing a conversion operation.

51. A device according to claim 50, wherein said limit signal generated by controller instructs the lowering of the clock speed of the microcomputer.

52. A device according to claim 50, wherein said limit signal generated by controller instructs the stopping of the operation of the microcomputer.

53. A device according to claim 42, wherein the image pickup device obtains a fundus image of the examined eye.

54. A device according to claim 42, wherein the signal converter generates a signal-converter limit signal when the signal converter performs a conversion operation, instructing said controller to generate said limit signal, wherein said controller generates said limit signal in response to receiving the signal-converter limit signal.

55. A device according to claim 54, wherein the illuminator comprises an observation light source, wherein the ophthalmological apparatus further comprises a strobe light source, connected to said controller, a strobe-light-source charging circuit, connected to the strobe light source and said controller, connected to charge the strobe light source, an observation-light-source charging circuit, connected to the observation light source and said controller, configured to power the observation light source, a switch, an external device, connected via the switch to said controller, a system power supply, connected to said controller, including a switching power supply and a battery power supply, a display device, connected to said controller, configured to display images picked up by the image pickup device, and an inverter power supply, connected to the display device and to said controller, configured to supply power to the display device, wherein said controller comprises a microcomputer, wherein said controller generates a plurality of limit signals in response to receiving said limit signal from the signal converter, wherein one of said controller limit signals instructs the strobe-light-source charging circuit to stop charging the strobe light source while the signal converter is performing the conversion operation, wherein another one of said controller limit signals instructs the observation-light-source charging circuit to stop charging the observation light source while the signal converter is performing the conversion operation, wherein another one of said controller limit signals instructs said microcomputer to either operate at a reduced clock frequency, lower than that used when the signal converter is not performing a conversion operation, or stop its operation while the signal converter is performing the conversion operation, wherein another one of said controller limit signals instructs the switch to electrically disconnect the external device from said controller while the signal converter is performing the conversion operation, wherein another one of said controller limit signals instructs the system power supply to switch to the use of the battery power supply to supply power to the ophthalmological apparatus while the signal converter means is performing the conversion operation, and wherein another one of said controller limit signals instructs the inverter power supply to stop supplying power to the display device while the signal converter means is performing the conversion operation.

56. A method of reducing noise produced during an eye examination with an ophthaletological apparatus that illuminates the eye to be examined, forms an image of the illuminated, examined eye, and generates a signal representing the image, converts the signal to digital data by a conversion operation, and performs at least one additional process with at least one additional element, said noise reducing method comprising the step of:

limiting a predetermined operation of at least one of the illuminating operation and the performing of at least one additional process by the ophthalmological apparatus step while the ophthalmological apparatus converts the signal to digital data, thereby reducing noise generated during at least one of the illuminating operation and the performing of at least one additional process.

57. A method according to claim 56, wherein said apparatus also supplies power to a light source and emits light with the light source, wherein said limiting step limits the power supplied to the light source while the ophthalmological apparatus converts the signal to digital data.

58. A method according to claim 57, wherein the light source is a strobe light source, and wherein said limiting step comprises the step of limiting the power supplied to the strobe light source.

59. A method according to claim 56, wherein the ophthalmological apparatus also displays the formed image, wherein said limiting step limits the displaying of the image while the ophthalmological apparatus converts the signal to digital data.

60. A method according to claim 59, wherein the ophthalmological apparatus displays the images with a display device to which power is supplied, wherein said limiting step stops the supply of power to the display device while the ophthalmological apparatus converts the signal to digital data.

61. A method according to claim 56, wherein the ophthalmological apparatus also performs an operation relating to the examining of the eye with an external device, external to the ophthalmological apparatus, wherein said limiting step electrically disconnects the external device from the ophthalmological apparatus while the ophthalmological apparatus converts the signal to digital data while ophthalmological apparatus converts the signal to digital data.

62. A method according to claim 56, wherein the ophthalmological apparatus uses alternating current electrical power to perform at least one of the illuminating, the image forming, the converting, and the performing at least one additional process with at least one additional element, and wherein said limiting step stops the use of alternating current and causes battery power to perform said at least one of the illuminating, the image forming, the converting, and the performing at least one additional process with at least one additional element while the ophthalmological apparatus converts the signal to digital data.

63. A method according to claim 56, wherein at least one of the illuminating, the image forming, the converting, and the performing at least one additional process with at least one additional element are controlled with a microcomputer, wherein said limiting step limits the operation of the microcomputer means while the ophthalmological apparatus converts the signal to digital data.

64. A method according to claim 63, wherein said limiting step lowers the clock speed of the microcomputer while the ophthalmological apparatus converts the signal to digital data.

65. A method according to claim 63, wherein said limiting step stops the operation of the microcomputer while the ophthalmological apparatus converts the signal to digital data.

66. A method according to claim 28, wherein the ophthalmological apparatus forms a fundus image of the examined eye, wherein said ophthalmological apparatus converts the signal to digital data with a signal converter, wherein said limiting step is performed in response to the generation of a limit signal by the signal converter.

67. A method according to claim 66, wherein the ophthalmological apparatus also includes an observation light source, a strobe light source, a switch connecting and disconnecting an external device thereto, a system power supply supplying switching power and battery power to the ophthalmological apparatus, a display device displaying the formed images, and a microcomputer, wherein said limiting step comprises the steps of:

stopping the charging of the strobe light source while the ophthalmological apparatus converts the signal to digital data, stopping the charging of the observation light source while the ophthalmological apparatus converts the signal to digital data, limiting the operation of the microcomputer to either operate at a reduced clock frequency, lower than that used when the conversion operation is not performed, or stop its operation while the ophthalmological apparatus converts the signal to digital data, electrically disconnecting the external device from the ophthalmological apparatus while the ophthalmological apparatus converts the signal to digital data, supplying the ophthalmological apparatus with battery power while the ophthalmological apparatus converts the signal to digital data, and stopping the supply of power to the display device while the ophthalmological apparatus converts the signal to digital data.

* * * * *

UNITED STATES PATENT AND TRADEMARK OFFICE
CERTIFICATE OF CORRECTION

PATENT NO. : 6,550,916 B1
DATED : April 22, 2003
INVENTOR(S) : Kyoji Sekiguchi

It is certified that error appears in the above-identified patent and that said Letters Patent is hereby corrected as shown below:

Column 12,
Line 38, "claim 15" should read -- claim 15, --.

Column 17,
Line 27, "ophthalefological" should read -- opthamological --.

Column 18,
Line 31, "claim 28," should read -- claim 56, --.

Signed and Sealed this

Eighteenth Day of November, 2003

JAMES E. ROGAN
*Director of the United States Patent and Trademark Office*